（12） United States Patent
Lanzavecchia et al.

US009347043B2

(10) Patent No.: US 9,347,043 B2
(45) Date of Patent: May 24, 2016

(54) METHODS FOR PRODUCING ANTIBODIES FROM PLASMA CELLS

(75) Inventors: Antonio Lanzavecchia, Bellinzona (CH); David Jarrossay, Bellinzona (CH)

(73) Assignee: Institute for Research in Biomedicine, Bellinzona (CH)

( * ) Notice: Subject to any disclaimer, the term of this patent is extended or adjusted under 35 U.S.C. 154(b) by 0 days.

(21) Appl. No.: 12/604,240

(22) Filed: Oct. 22, 2009

(65) Prior Publication Data
US 2010/0145031 A1 Jun. 10, 2010

Related U.S. Application Data

(63) Continuation-in-part of application No. 12/509,731, filed on Jul. 27, 2009.
(60) Provisional application No. 61/181,582, filed on May 27, 2009.

(30) Foreign Application Priority Data

Oct. 22, 2008 (GB) .................................. 0819376.5

(51) Int. Cl.
| C12N 5/00 | (2006.01) |
| C12N 5/02 | (2006.01) |
| C12N 5/0781 | (2010.01) |
| C07K 16/00 | (2006.01) |
| C07K 16/10 | (2006.01) |
| C07K 16/12 | (2006.01) |

(52) U.S. Cl.
CPC .............. *C12N 5/0635* (2013.01); *C07K 16/00* (2013.01); *C07K 16/1018* (2013.01); *C07K 16/1282* (2013.01); *C07K 2317/21* (2013.01); *C12N 2502/1394* (2013.01)

(58) Field of Classification Search
None
See application file for complete search history.

(56) References Cited

U.S. PATENT DOCUMENTS

| 6,300,064 | B1 | 10/2001 | Knappik | |
| 7,202,343 | B2 * | 4/2007 | Gudas et al. | 530/387.1 |
| 7,318,925 | B2 * | 1/2008 | Roskos et al. | 424/145.1 |
| 7,368,256 | B2 * | 5/2008 | Schmechel et al. | 435/7.32 |
| 2011/0124552 | A1 * | 5/2011 | Galipeau et al. | 514/4.8 |

FOREIGN PATENT DOCUMENTS

| WO | 2004016769 A2 | 2/2004 |
| WO | 2007134327 A2 | 11/2007 |
| WO | 2008028946 A2 | 3/2008 |
| WO | 2008066691 A2 | 6/2008 |
| WO | 2008110937 A2 | 9/2008 |

OTHER PUBLICATIONS

Wrammert et al Nature, 2008, V.453, pp. 667-672.*
Meijer et al., J Mol. Biol. 2006, v.358, pp. 764-772.*
Cuneo et al. Cancer Genet Cytogen, 1996, v.90, pp. 171-175).*
Cassese et al ( J of Immunol., 2003,171,1684-1690).*
Tiller, et al, J Immunol Methods 2008 329:112-124.
Harriman, William, J Immunol Methods 341; 135-145 2009.
Jin, et al, Nat Medicine 15; 1088 2009.
Arce, Sergio, CD38 low IgG-secreting cells are precursors of various CD38 high-expressing plasma cell populations. J Leukoc Biol 75:1022-1028. 2004.
Bernasconi, Nadia, Maintenance of serological memory by polyclonal activation of human memory B cells. Science 298:2199-2202, 2002.
Bieback, Critical parameters for the isolation of mesenchymal stem cells from umbilical cord blood. Stem Cells 22:625-634, 2004.
Cassese, Plasma cell survival is mediated by synergistic effects of cytokines and adhesion-dependent signals. J Immunol 171:1684-1690, 2003.
Dexter, Growth and differentiation in the hemopoietic system. Annu Rev Cell Biol 3:423-441, 1987.
Geffroy-Luseau, Osteoclasts support the survival of human plasma cell in vitro. Int Immunol 20:775-782, 2008.
Kawano, Identification of immature and mature myeloma cells in the bone marrow of human myelomas. Blood 82:564-570, 1993.
Lanzavecchia, A, Human monoclonal antibodies by immortalization of memory B cells. Curr Opin Biotechnol 18:523-528, 2007.
Manabe, Bone marrow-derived stromal cells prevent apoptotic cell death in B-lineage acute lymphoblastic leukemia. Blood 79:2370-2377, 1992.
Manz, Lifetime of plasma cell in the bone marrow. Nature 388:133-134, 1997.
Manz, Survival of long-lived plasma cell is independent of antigen. Int Immunol 10:1703-1711, 1998.
Meijer, Isolation of human antibody repertoires with preservation of the natural heavy and light chain pairing. J Mol Biol 358:764-772, 2006.
Merville, Bcl-2+ tonsillar plasma cell are rescued from apoptosis by bone marrow fibroblasts. J Exp Med 183:227-236, 1996.
Mihara, Development and functional characterization of human bone marrow mesenchymal cells immortalized by enforced expression of telomerase. Br J Haematol 120:846-849, 2003.

(Continued)

*Primary Examiner* — Michail Belyavskyi
(74) *Attorney, Agent, or Firm* — Dennis A. Bennett

(57) ABSTRACT

The invention relates to methods of producing antibodies, including monoclonal antibodies, comprising culturing a limited number of plasma cells. It also relates to methods of identifying antibodies by performing assays on the antibodies produced by the cultured plasma cells to determine their function, binding specificity, epitope specificity, and/or their ability to neutralize a toxin or a pathogen. The invention also relates to antibodies and antibody fragments produced by the methods of the invention as well as methods of using the antibodies and antibody fragments.

21 Claims, 6 Drawing Sheets

(56) References Cited

OTHER PUBLICATIONS

Minges Wols, The role of bone marrow-derived stromal cells in the maintenance of plasma cell longevity. J Immunol 169:4213-4221, 2002.
Pihlgren, Reduced ability of neonatal and early-life bone marrow stromal cells to support plasmablast survival. J Immunol 176:165-172, 2006.
Pittenger, Multilineage potential of adult human mesenchymal stem cells. Science 284:143-147, 1999.
Radbruch, Competence and competition: the challenge of becoming a long-lived plasma cell or . Nat Rev Immunol 6:741-750, 2006.
Shapiro-Shelef, Regulation of plasma-cell development. Nat Rev Immunol 5:230-242, 2005.
Slifka, immunity due to long-lived plasma cells. Immunity 8:363-372, 1998.
Sotiropoulou, Characterization of the optimal culture conditions for clinical scale production of human mesenchymal stem cells. Stem Cells 24:462-471, 2006.
Tarlinton, Plasma cell or differentiation and survival. Curr Opin Immunol 20:162-169, 2008.
Traggiai, An efficient method to make human monoclonal antibodies from memory B cells: potent neutralization of SARS coronavirus. Nat Med 10:871-875, 2004.
Wardemann, Predominant autoantibody production by early human B cell precursors. Science 301:1374-1377, 2003.
Williamson, Human monoclonal antibodies against a plethora of viral pathogens from single combinatorial libraries. Proc Natl Acad Sci U S A 90:4141-4145, 1993.
Wrammert, Rapid cloning of high-affinity human monoclonal antibodies against influenza virus. Nature 453:667-671, 2008.
Wrammert, Rapid cloning of high-affinity human monoclonal antibodies against influenza virus. Nature 453:667-671., 2008, Supplemental information.
International Search Report for Int'l Application No. PCT/IB2009/007375, corresponding international application. Date mailed: Sep. 4, 2010.
Cuneo, et al, Cancer Genet Cytogen, v.90, p. 764-772, 2006.
Dominici, Minimal criteria for defining multipotent mesenchymal stromal cells. The International Society for Cellular Therapy position statement. Cytotherapy 8:315-317, 2006.
Smirnov, Y, Arch Virol, v145, No. 8, 1733-1741, 2000.
Holt, Trends in Biotech., v21, No. 11, 484-490, 2003.
Davies, Immunotechnology, v 2, No. 3, 169-179, 1996.
Little, Immunology Today, v 21, No. 8, 364-370, 2000.
Borrebaeck, Biotechnology, v 10, No. 6, 697-698, 1992.
Love, J. C., et al: "A microengraving method for rapid selection of single cells producing antigen-specific antibodies", Nature Biotechnolgy, Nature Publishing Group, New York, NY, US, vol. 24, No. 6, Jun. 1, 2006, pp. 703-707.
Poulsen, Tine Rugh et al: "Kinetic, affinity, and diversity limits of human polyclonal antibody responses against tetanus toxoid", The Journal of Immunology, The American Association of Immunologists, US, vol. 179, No. 6, Sep. 1, 2007, pp. 3841-3850.
Wols, Heather a Minges, et al: "The effects of microenvironment and internal programming on plasma cell survival", International Immunology, Oxford University Press, GB, vol. 19, No. 7, Jul. 1, 2007, pp. 837-846.
The ISR and Written Opinion issued in the parent/corresponding PCT case (mailed on Oct. 27, 2010).

* cited by examiner

METHODS FOR PRODUCING ANTIBODIES FROM PLASMA CELLS

This application claims priority to GB Application No. 0819376.5, filed Oct. 22, 2008, and U.S. Provisional Application Ser. No. 61/181,582, filed May 27, 2009, and is a continuation-in-part of U.S. application Ser. No. 12/509,731, filed Jul. 27, 2009, the disclosures of which are hereby incorporated by reference, as if written herein, in their entireties.

BACKGROUND

Plasma cells are terminally differentiated, non-proliferating cells, which secrete antibodies at very high rate (thousands of molecules per second corresponding to about 30-50 pg per cell per day).

The isolation of antibodies, for example monoclonal antibodies, from plasma cells relies on cloning and expression of the immunoglobulin genes. This can be done using phage display libraries of scrambled VH and VL genes isolated from plasma cells, or, by isolation of paired VH and VL genes from single plasma cells using single cell PCR. However, in order to screen the antibodies produced by plasma cells the immunoglobulin genes need to be cloned and expressed in a recombinant form in order to determine specificity and functional properties of the encoded antibody. This method is cumbersome, expensive, time-consuming, not adaptable to high-throughput and inefficient at retrieving rare antibodies that are produced by a minor fraction of the total repertoire of plasma cells.

Accordingly, there is a need to identify a more efficient method that is adaptable to high-throughput for the isolation and screening of antibodies, for example monoclonal antibodies, from plasma cells.

SUMMARY

The invention is based, in part, on the discovery of an efficient and high-throughput method of producing antibodies from plasma cells that enables characterization of the antibodies without relying on cloning and expression of the immunoglobulin genes. The antibodies produced using the present invention can be characterized by performing multiple screens, including binding, functional and/or neutralization assays. The invention provides a method for the identification of rare antibodies produced by plasma cells.

Accordingly, in one aspect of the invention, the invention provides a method of producing an antibody from plasma cells comprising culturing the plasma cells in limited numbers. In one embodiment, the invention provides a method of producing a monoclonal antibody from plasma cells comprising culturing the plasma cells in single cell cultures. The methods of the invention may further comprise characterisation of the antibodies or antibody fragments. Characterization of the antibodies or antibody fragments include, but are not limited to, performing functional assays to determine the function of the antibody or antibody fragment, binding assays to determine the binding specificity of the antibody or antibody fragment or the epitope recognized by the antibody or antibody fragment, and/or neutralization assays to determine the ability of the antibody or antibody fragment to neutralize a toxin or a pathogen.

In another embodiment, the invention provides a method of producing an antibody or an antibody fragment. The method comprises culturing a limited number of plasma cells, identifying cultures producing an antibody with a desired characteristic, isolating nucleic acid encoding the antibody produced, and expressing the nucleic acid in a host cell.

In another aspect of the invention, the invention provides an isolated antibody or an antibody fragment produced by a method of the invention. The invention also provides methods of diagnosing and/or treating a variety of conditions or diseases using the isolated antibodies or antibody fragments of the invention.

DETAILED DESCRIPTION OF THE INVENTION

Figure 1:
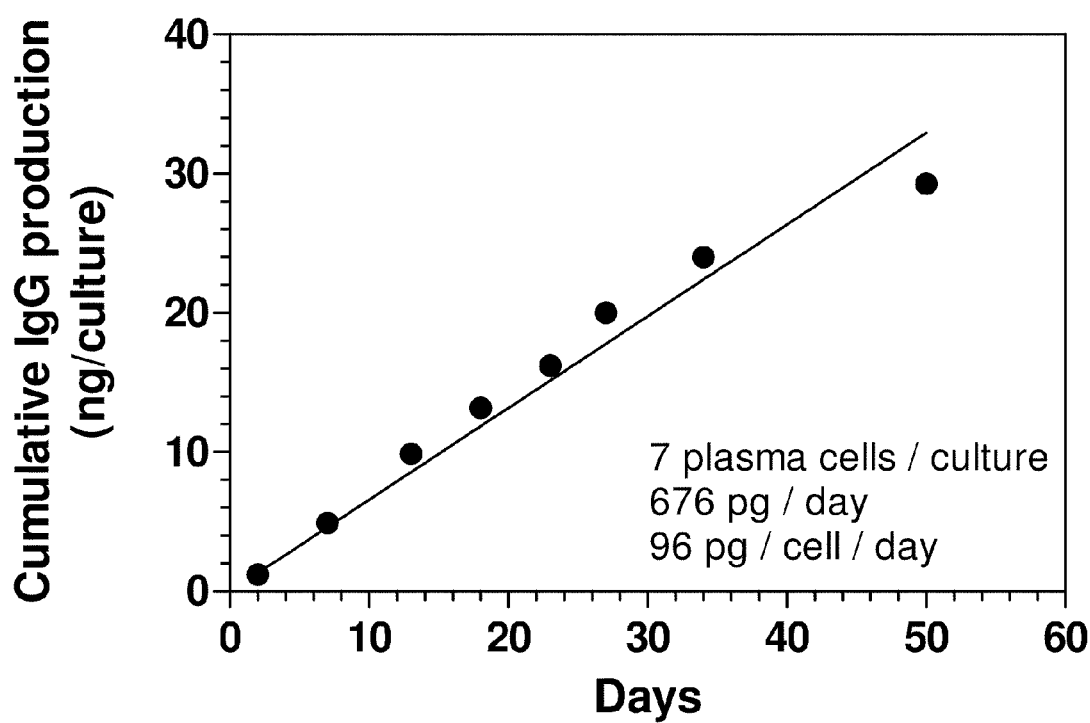
FIG. 1 shows the cumulative production of IgG by CD138+ plasma cells isolated from peripheral blood and cultured on monolayers of mesenchymal stromal cells for 50 days.

The invention is based on the discovery of an efficient and high-throughput method of producing antibodies from plasma cells that enables characterization of the antibodies without relying on cloning and expression of the immunoglobulin genes. In one aspect the invention provides a method of producing an antibody from plasma cells comprising culturing the plasma cells in limited numbers. The antibodies produced using the present invention can be characterized conveniently with multiple screens, including binding, functional and/or neutralization assays, and that can even be performed in situ, i.e., in the wells in which the plasma cells were cultured.

As used herein, the term "plasma cell" includes all primary antibody secreting cells (ASCs) that are found in peripheral blood, bone marrow, tissues or body fluids, or are generated in vitro from B cells. Recently generated plasma cells are referred to as "plasma blasts." Naturally generated plasma blasts are generally found in blood, particularly peripheral blood. Plasma blasts can also be generated in vitro, by stimulating B cells with a variety of stimuli including polyclonal activators such as TLR agonists. Herein, the term "plasma cell" or "plasma cells" shall be considered to include both "plasma cells," "plasma blasts" and ASCs.

Theoretically, any number of plasma cells can be cultured in the culture medium to produce and identify an antibody of desired characteristic. Practically, the number of plasma cells that can be cultured is limited by the technology available to clone and express the multiple VH and VL gene sequences and combination thereof present in the polyclonal cell culture. In one embodiment, "limited number of plasma cells" refers to a number of plasma cells that is about 100 or less, e.g., 90 or less, 80 or less, 70 or less, 60 or less, 50 or less, 45 or less, 40 or less, 35 or less, 30 or less, 25 or less, 20 or less, 17 or less, 15 or less, 12 or less, 10 or less, 9 or less, 8 or less, 7 or less, 6 or less, 5 or less, 4 or less, 3 or less, 2 or less, or 1 or less.

In one embodiment, the invention provides a method of producing an antibody from plasma cells comprising culturing the plasma cells at low concentration of plasma cells per culture. A low concentration of plasma cells per culture generally comprises about 1 to about 10, or about 1 to about 15, or about 1 to about 20, or about 1 to about 25, or about 1 to about 30, or about 1 to about 40, or about 1 to about 50, or about 1 to about 60, or about 1 to about 70, or about 1 to about 80, or about 1 to about 90, or about 1 to about 100 cells per culture.

In another embodiment, the invention provides a method of producing an antibody from plasma cells comprising culturing the plasma cells, wherein the plasma cells have been diluted to a low concentration of cells per culture. In yet another embodiment, the invention provides a method of producing an antibody from plasma cells comprising culturing reduced numbers of plasma cells. The number of plasma cells isolated, for example, from a biological source, can be reduced as described below. As used herein, "reduced number of plasma cells" is used interchangeably with "limited number of plasma cells" as described above.

Techniques of obtaining the number of desired cells in a culture are well known in the art. Such techniques include, but are not limited to, limiting dilution, or cell sorting and deposition. For example, cultures comprising a limited or reduced number of plasma cells can be achieved by single cell deposition using a cell sorter or by diluting a suspension of plasma cells with enough culture medium such that 1, 2, 3 or more cells, for example 5, 10, 15, 20, 25, 30, 40, 50, 60, 70, 80, 90 or 100 cells are present per well of a microtiter culture plate.

In one embodiment, a single plasma cell is cultured. Given the monoclonal nature of the antibodies produced by a single plasma cell, culturing plasma cells in single cell culture would produce a monoclonal antibody population. Thus, in one embodiment, the invention provides a method of producing a monoclonal antibody from plasma cells comprising culturing the plasma cells in single cell cultures.

As used herein, a "single cell culture" is used interchangeably with "culturing a single plasma cell" and relates to a culture comprising, on average, a single plasma cell. Thus in a multi-well plate, e.g., a 96-well, a 384-well plate or a 1536-well plate, most of the wells will contain a single plasma cell, some will contain no plasma cells and some others will contain more than one plasma cell. In some embodiments, the plasma cells can be cultured in cultures where there is, on average, less than 1 cell per well, e.g., 0.8 cells/well, 0.6 cells/well, 0.5 cells/well, 0.3 cells/well or 0.1 cells/well. Techniques of obtaining a single cell in a culture are similar to those described above, except that now an average of 1 or less than 1 cells is present per well of a microtiter culture plate.

The invention further provides a method of producing an antibody or an antibody fragment. The method comprises culturing a limited number of plasma cells according to any method of the invention, identifying cultures producing an antibody with a desired characteristic, isolating nucleic acid encoding the antibody produced, and expressing the nucleic acid in a host cell.

Unlike memory B cells, which can be expanded into clones of antibody producing cells by immortalization (Traggiai et al., 2004, *Nat Med* 10:871-875; Lanzavecchia et al, 2007, *Curr Opin Biotechnol.* 18:523-528), plasma cells do not divide, and cannot be stimulated or immortalised. Therefore, in order to harness the use of these "antibody factories" in any meaningful way, the plasma cell must be maintained alive in culture. Plasma cells produce and secrete antibodies in a continuous manner, and the size of the antibody population therefore increases as a function of time. Although plasma cells survive for very long periods in vivo, they do not survive for much longer than a day in vitro (experimental data not shown). Accordingly, the invention provides a method of producing antibodies by culturing plasma cells, including, but not limited to, a single plasma cell, in a culture medium that comprises an exogenous component or components that prolongs survival of the cultured plasma cells.

In general, the survival of the cultured plasma cells is prolonged for sufficient time such that the antibody is produced in quantities needed for characterization of the antibody, i.e., the culture medium contains sufficient antibodies that it can be used for screening assays, including, but not limited to, binding assays, neutralization assays or other assays that determine the function, or otherwise characterize the antibodies. The cultures containing an antibody of the desired specificity can be then isolated and the immunoglobulin genes can be amplified, sequenced and expressed to produce a monoclonal antibody.

The survival of the plasma cells, including, but not limited to, a single plasma cell, in culture may be prolonged for a short term or a long term. As used herein, "short term" refers to a period of at least two days, to about 9 days, i.e., 2, 3, 4, 5, 6, 7, 8, or about 9 days. As used herein, "long term" refers to a period of at least ten days, e.g., 10, 15, 20, 25, 30, 35, 40, 45, 50, 60, 70, 80, 90, 100, 110, 120, 130, 140, or about 150 days.

Although prolonging the survival of the plasma cells for a short term may not produce as many antibodies as that produced when the survival of the plasma cells is prolonged for a long term, prolonging the survival of the plasma cells for a short term, as described herein, is easier, quicker and more economical and is particularly useful for screening the antibodies in assays that are sensitive. Prolonging the survival of the plasma cells for a long term is particularly suitable in those circumstances where characterization of antibodies requires multiple screening assays or assays of low sensitivity.

In one embodiment, the exogenous component present in the culture medium prolongs survival of the cultured plasma cells for a short term. In another embodiment, the exogenous component prolongs survival of the cultured plasma cells for a long term. The exogenous component can be one or more ligands for a receptor expressed by the plasma cell or one or more non-plasma-cells.

Examples of ligands for a receptor expressed by the plasma cells useful for prolonging survival of the cultured plasma cells include, but are not limited to, cytokines, chemokines and other ligands. In one embodiment, the ligand is IL-5, IL-6, stromal cell-derived factor-1 (SDF-1), TNF-α, or a ligand for CD44, e.g., ialuronic acid. In another embodiment, the exogenous component comprises one or more ligands selected from the group consisting of IL-5, IL-6, stromal cell-derived factor-1 (SDF-1), TNF-α, ligands for CD44, e.g., ialuronic acid, and combinations thereof and is useful for prolonging survival of the cultured plasma cells for a short term or a long term.

Examples of non-plasma cells useful for prolonging survival of the cultured plasma cells include, but are not limited to, mesenchymal stromal cells, fibroblasts or osteoclasts. In one embodiment, the non-plasma cells are mesenchymal stromal cells, fibroblasts or osteoclasts, and are useful for prolonging survival of the cultured plasma cells for a short term or a long term. In another embodiment, the non-plasma cells are mesenchymal stromal cells and are useful for prolonging survival of the cultured plasma cells for a short term or a long term. The mesenchymal stromal cells can be mammalian mesenchymal stromal cells, including, but not limited to, human mesenchymal stromal cells. The mesenchymal stromal cells may, optionally, be immortalised prior to use in the culture.

In one embodiment of the invention, the plasma cells are cultured, for example, in a single cell culture, for about 3 to about 7 or about 5 to about 9 days in culture in the presence of one or more ligands for a receptor expressed by the plasma cell. In another embodiment, the plasma cells are cultured, for example, in a single cell culture, for about 5 to 7, or about 10, or about 15, or about 20, or about 25, or about 30, or about 35, or about 40, or about 45, or more than 50 days in culture in the presence of one or more types of non-plasma-cells. In yet another embodiment, the plasma cells are cultured, for example, in a single cell culture, for about 5-7, or about 10, or about 15, or about 20, or about 25, or about 30, or about 35, or about 40, or about 45, or more than 50 days in culture in the presence of mesenchymal stromal cells. In yet another embodiment, the plasma cells are cultured, for example, in a single cell culture, for about 5-7, or about 10, or about 15, or about 20, or about 25, or about 30, or about 35 or about 40, or about 45 or about 50, or about 55 or about 60, or about 65, or more than 70 days in culture in the presence of one or more types of non-plasma cells and one or more ligands for a receptor expressed by the plasma cell.

In one embodiment, the plating efficiency of the cultured cells may be at least about 30%, in another embodiment the plating efficiency may be at least about 40%, in another embodiment the plating efficiency may be at least about 50%, in another embodiment the plating efficiency may be at least about 55%, in another embodiment the plating efficiency may be at least about 60% or more.

As used herein, the term "plating efficiency" relates to the percentage of plasma cells that survive long enough to produce detectable amounts of antibody in the supernatant.

The plasma cells that are cultured can be obtained from any desired species. In one embodiment, the plasma cells are mouse, rat, rabbit, camel, or monkey plasma cells. In another embodiment, the cultured plasma cells are human plasma cells and the antibodies produced are human antibodies. In yet another embodiment, human monoclonal antibodies are produced by culturing human plasma cells in single cell cultures.

Plasma cells, for example human plasma cells may be isolated from the peripheral blood of a human. These human plasma cells may be referred to as "peripheral blood plasma cells" or "circulating plasma cells." Plasma cells, for example human plasma cells may also be isolated from the bone marrow, tissues or from body fluids, including but not limited to synovial fluid, cerebrospinal fluid and exudates, of a human. The term "tissue" is intended to cover any tissue present within the human body, and may include cardiac tissue, nervous tissue, muscular tissue, epithelium, connective tissue and lymphoid organs such as thymus, spleen and lymph nodes.

Plasma cells are generally characterised by the expression of CD138, and optionally by the additional expression of CD27, CD38, CD9, CD44 and MHC class II molecules. In one embodiment, the cells may be isolated from peripheral blood, tissues, bone marrow or body fluids according to the expression of CD138. Surface markers such as CD27, CD38, CD9, CD44 and MHC class II molecules may also be used in addition to CD138 to improve the isolation procedure and to identify plasma cell subsets (Arce et al., 2004, J Leukoc Biol, 75:1022-1028). In another embodiment, the plasma cells may be isolated using magnetic micro-beads. In yet another embodiment, the plasma cells may be isolated using magnetic micro-beads which are coated with immobilised anti-CD138 antibodies. In still another embodiment, enrichment of the plasma cells using magnetic micro-beads may be followed by cell sorting.

In one embodiment, the plasma cells may be isolated from the peripheral blood of a human donor following vaccination. Vaccination refers to the administration of any antigen capable of inducing an immune response. The vaccine may be any vaccine now known, or later available to one of skill in the art and includes, but is not limited to, tetanus toxoid, influenza, yellow fever, tetanus-diphtheria, hepatitis B, small pox and cancer vaccines. In another embodiment, the vaccination may be a booster vaccination. The plasma cells may be isolated from the donor 4, 5, 6, 7, 8, 9, 10 or more days after the vaccination. In one embodiment, the plasma cells may be isolated from a donor that is responding to a known pathogen. In another embodiment, the plasma cells may be isolated from a donor that is responding to an unknown pathogen. In a further embodiment the plasma cells may be isolated from a donor with an allergy. In yet another embodiment the plasma cells may be isolated from a donor under steady state conditions. In still another embodiment the plasma cells may be isolated from a donor with an autoimmune disease.

In another embodiment, the plasma cells may be generated in vitro by the stimulation of B cells. This stimulation may be performed by any method known in the art including polyclonal or antigen-specific stimulation of naïve or memory B cells (Bernasconi et al, 2002, *Science*, 298:2199-2202).

The method of the present invention may be used to culture plasma cells secreting any antibodies of any isotype. In one embodiment the plasma cells may be IgG plasma cells, in another embodiment the plasma cells may be IgA plasma cells, in another embodiment the plasma cells may be IgM plasma cells, in another embodiment the plasma cells may be IgD plasma cells, and in a further embodiment the plasma cell may be IgE plasma cells. In yet another embodiment, the isolated population of plasma cells may be a mixed population of plasma cells comprising two or more isotypes.

The isolated human plasma cells may be counted using an enzyme linked immunosorbent spot (ELISPOT) assay (Bernasconi et al, 2002, *Science*, 298:2199-2202). This assay works by visualising a product secreted by the cell of interest, whereby each spot produced by the assay represents a single cell.

In one embodiment, the human plasma cells may be seeded as single cell by limiting dilution or by single cell deposition. In one aspect the human plasma cells may be seeded as single cells in the presence of mesenchymal stromal cells. In another embodiment, the human plasma cells may be seeded as a polyclonal culture. The plasma cells may be seeded as a polyclonal cell culture in the presence of mesenchymal stromal cells. The polyclonal human plasma cell culture may, alternatively, be separated into single cell culture using limiting dilution. In another aspect the polyclonal human plasma cell culture may be separated into single cell culture using single cell deposition.

Mesenchymal stromal cells are fibroblast-like cells, but have a greater differentiation potential than fibroblasts, and are capable of differentiating into osteoblasts, chondrocytes and fat cells. Mesenchymal stromal cells are found as heterologous populations, and form the supportive structure of the tissue in which they reside. In the bone marrow, mesenchymal stromal cells are required for growth and differentiation of hematopoietic cells and for maintenance of leukemic cells. Primary mesenchymal stromal cells can be isolated in appropriate media and cultured for several passages however only for a limited time before undergoing senescence. Transduction with telomerase reverse transcriptase (TERT) has been used to immortalize mesenchymal stromal cells that expand indefinitely in vitro while maintaining their physiological growth rate and functional characteristic.

The mesenchymal stromal cells used in the cultures may be bone marrow-derived mesenchymal stromal cells. The mesenchymal stromal cells may be mammalian mesenchymal stromal cells, e.g., human mesenchymal stromal cells. Mesenchymal stromal cells for use in the methods of the invention may be isolated from adherent bone marrow cells by culture in an appropriate media. This media may contain hydrocortisone. Mesenchymal stromal cells may also be derived from other tissues.

For practical reasons, mesenchymal stromal cells may be immortalised prior to use in the methods of the invention. As used herein, "immortalised" means that the mesenchymal stromal cells have improved proliferative capacity while maintaining all the characteristics that make them capable of sustaining plasma cells, including the capacity to undergo contact dependent inhibition of growth. In one embodiment, the mesenchymal stromal cells may survive for at least about 1 week after having reached confluence. In another embodiment, the immortalised mesenchymal stromal cells may survive for at least about 2 weeks after having reached confluence, or for at least about 3 weeks after having reached confluence, or for at least about 4 weeks or more after having reached confluence.

The mesenchymal stromal cells may be immortalised by any means known in the art. In one embodiment, the mesenchymal stromal cells are immortalised by transduction with the telomerase reverse transcriptase gene. In another embodiment, the mesenchymal stromal cells may be immortalised by transduction with the TERT gene according to the method described in Mihara et al., 2003 *Br J Haematol* 120: 846-849.

As discussed above, the invention provides a method of producing an antibody or an antibody fragment. The method comprises culturing a limited number of plasma cells, identifying cultures producing an antibody with a desired characteristic, isolating nucleic acid encoding the antibody produced, and expressing the nucleic acid in a host cell.

As used herein, the terms "fragment" and "antibody fragment" are used interchangeably to refer to any fragment of an antibody of the present invention. In one embodiment, the antibody fragment retains the antigen-binding activity of the antibody. In another embodiment, an antibody fragment may comprise 10, 20, 30, 40, 50, 60, 70, 80, 90, 100, 150, 200, 300, 400, 500, 600, 700, 800, 900 or 1000 or more consecutive amino acids. Exemplary antibody fragments may comprise one or more of Fc, Fab, Fab', F(ab')$_2$, Fv, scFv fragments, the heavy chain, the light chain, the hinge region, the antigen binding site, single chain antibodies or any portion thereof.

As used herein, the term "nucleic acid" encompasses all forms of nucleic acid, including but not limited to genomic DNA, cDNA, and mRNA. Cloning and heterologous expression of the antibody or antibody fragment can be performed using conventional techniques of molecular biology and recombinant DNA, which are within the skill of the art (Wrammert et al., 2008 *Nature* 453, 667-671 & Meijer et al., 2006 *J Mol Biol* 358, 764-772). Such techniques are explained fully in the literature, for example in Sambrook, 1989 *Molecular Cloning; A Laboratory Manual, Second Edition*. For retrieval of VH/VL sequences and expression the method of Tiller et al., *J Immunol Methods* 2008 329:112-124, can be used.

In one embodiment, the antibody is expressed using an appropriate vector or virus in a eukaryotic cell. The eukaryotic cell may be a CHO, 293T, 293 F, or a yeast cell. In another embodiment, the antibody is expressed using an appropriate vector or phage in a prokaryotic cell. The prokaryotic cell may be a bacterial cell, e.g., an *E. coli* cell. In a further embodiment, the heterologous expression system may be a cell free system.

The antibodies and antibody fragments produced by the methods of the invention can easily be isolated using well established methodologies (Coligan et al Eds *Current Protocol in Immunology* 1: 2.7). In one embodiment, the antibodies or antibody fragments, including the monoclonal antibodies or antibody fragments, of the invention may be isolated from the culture supernatant by centrifugation or by affinity chromatography. In another embodiment, the antibodies or antibody fragments may be isolated according to their binding specificity. For example, the antibodies may be isolated by being applied to a solid support comprising appropriate immobilised antigen. In a further embodiment, the antibodies may be isolated using an anti-IgG, -IgE, -IgA, -IgD or -IgM antibody, which may, in some instances, be immobilised.

Plasma secreting Ig or specific antibodies can be isolated with an immunoaffinity method. Firstly, the secreted product may be captured onto the surface of the secretory cell, using appropriate covalently bound capturing reagents. Then the captured products may be revealed using a fluorescently labelled secondary antibody or antigen (Manz et al., 1998 *Int Immunol* 10, 1703-1711).

Antibody Characterisation

Plasma cells do not express surface immunoglobulin, and therefore cannot be selected according to isotype or antigen specificity. Antibodies produced by a plasma cell must therefore be isolated in order to be characterised. At present, there are two methods which are primarily used in the art to make human monoclonal antibodies from plasma cells. The first of these is to screen display libraries of antibodies prepared from total bone marrow of immune donors (Williamson et al., 1993 *Proc Natl Acad Sci USA* 90, 4141-4145). However this method is limited by the availability of bone marrow samples.

The second method involves the isolation of circulating plasma cells after a booster immunization followed by recovery of Ig genes from individual plasma cells using single cell PCR (Wrammert et al., 2008 *Nature* 453, 667-671 & Meijer et al., 2006 *J Mol Biol* 358, 764-772). This method is based on the fact that 6-8 days after a booster immunization a sizeable fraction of circulating plasma cells are specific for the immunizing antigen. This approach however requires extensive gene cloning and expression work to be performed before the antibody specificity can be assessed, and is therefore not very practical when the plasma cell response is directed against multiple antigens, such as complex pathogens. Development of a long-term culture system for human plasma cells is therefore particularly useful in order to retrieve enough antibody to perform in vitro binding assays, functional assays and further antibody characterisation, in order to be able to select the plasma cells that produce antibodies of interest.

Alternative methods to isolate antibodies from plasma cells or other antibody secreting cells are based on micromanipulation and include a first step wherein cells are plated in semisolid media (Harriman W D et al *J Immunol Methods* 341; 135-145 2009) or in microarray chips (Jin A et al *Nat Medicine* 15; 1088 2009) and the secreted antibodies are detected in situ using fluorescent probes. Once identified, the plasma cell is retrieved by micromanipulation and the VH and VL genes are amplified and sequenced. These methods, which are based on short term culture and local detection of secreted antibody, require special equipment for micromanipulation of antibody secreting cells and are not suitable to test the antibodies for functional properties such as virus or toxin neutralization. The methods of the present invention are not based on, nor do they require, any micromanipulation and allow the antibody that is produced to be screened in multiple assays, including, but not limited to, binding assays, functional assays and/or neutralization assays. In one embodiment, the invention provides a method of producing an antibody from plasma cells comprising culturing the plasma cells in limited numbers and characterizing the antibodies, wherein the method does not comprise micromanipulation to retrieve the antibody secreting plasma cells.

The invention includes the characterisation of the antibody or antibody fragment isolated by the methods of the invention. In one embodiment, antibody characterisation may comprise determining the binding specificity of the antibody or antibody fragment. In another embodiment, the antibody characterisation may comprise determining the epitope recognised by the antibody or antibody fragment. The binding specificity of an isolated antibody or antibody fragment and/or the epitope recognised by the antibody or antibody fragment may be determined by any means known in the art. In one embodiment, the binding specificity and/or recognised epitope may be determined by labelling the isolated antibody or antibody fragment, presenting the labelled antibody or antibody fragment to an antigen library, and detecting the labelled antibody or antibody fragment bound to its cognate antigen. In another embodiment, the labelled antibody or antibody fragment may be applied to a purification column containing immobilised antigen molecules, and the presence or absence of the labelled antibody or antibody fragments on the column may be used as an indication of antibody specificity and/or recognised epitope. It will be apparent to a person skilled in the art that plasma cells isolated from the peripheral blood of a donor who has been immunised with a particular antigen or has been exposed to a particular pathogen, will produce antibodies or antibody fragments which bind to that antigen or pathogen. Nevertheless, pathogens, particularly complex pathogens, are likely to comprise a number of antigens and the binding specificity and/or recognised epitope of a particular antibody or antibody fragment may still be ascertained.

The single cell culture method of the invention provides a single plasma cell producing a specific antibody from which the nucleic acid encoding the antibody can easily be isolated using well established methodologies (Wrammert et al., 2008 *Nature* 453, 667-671 & Meijer et al., 2006 *J Mol Biol* 358, 764-772). In one embodiment, the antibody characterisation may involve sequencing the nucleic acid encoding the antibody or antibody fragment. Nucleic acid sequencing may be performed by any method known in the art. In one embodiment, nucleic acid sequencing may be performed using the chain termination, wherein radioactive, fluorescent or other dyes may be used. In another aspect nucleic acid sequencing may be performed using an automated sequencing method.

In another embodiment, the characterisation may involve sequencing the antibody protein. The antibody protein may be sequenced by any method known in the art. In one embodiment, the antibody protein may be sequenced by N-terminal analysis, C-terminal analysis or Edman degradation. N-terminal analysis may comprise: i) reacting the protein with a reagent which will selectively label the amino terminal amino acid; ii) hydrolysing the protein; and iii) determining the amino terminal amino acid by chromatography and comparison with standards. Within this aspect, any labelling reagent may be used, including but not limited to Sanger's reagent, dansyl derivatives such as dansyl chloride, and phenylisothiocyanate. C-terminal analysis may comprise incubating the protein with a carboxypeptidase and taking samples at regular intervals to produce a plot of amino acid concentration versus time.

Following sequencing of the antibody protein, the invention also includes chemically synthesising a binding protein based on the identified antibody sequence. Chemical synthesis may be performed according to any method known in the art. In one embodiment, chemical synthesis may be performed by attaching the carboxy group of an amino acid to an insoluble solid support, and reacting the amino group of the immobilised antibody with the carboxy group of the next antibody in the sequence. This method can then be repeated until the required amino acid sequence has been produced, at which stage the complete protein may be cleaved from the solid support, and allowed or induced to adopt the correct protein fold.

The invention also includes antibodies or antibody fragments produced by any of the methods of the invention.

Pharmaceutical Uses of Antibody

The invention provides an antibody or antibody fragment produced by any of the methods of the invention for use in therapy, for example, for use in the treatment of allergy, infectious conditions or diseases, cancer and autoimmune conditions or diseases.

The term "allergy" includes all forms of hypersensitivity reaction caused by a non-parasitic antigen, including but not limited to allergic dermatitis, allergic rhinitis, angioedema, anaphylaxis, aspirin sensitivity, asthma, atopic dermatitis, bird allergy, canary allergy, cat allergy, chemical sensitivity, chicken allergy, conjunctivitis, chronic fatigue, contact dermatitis, cosmetic allergy, cows milk allergy, dermatitis, dog allergy, drug reaction, duck allergy, dust allergy, dust mite allergy, eczema, goose allergy, grass allergy, hayfever, headaches, heart irregularity, hives, hyperactivity in children, hypoglycaemia, respiratory and contact allergens, lactose intolerance, migraine headaches, milk allergy, mite allergy, nettle rash, parrot allergy, parakeet allergy, perennial rhinitis, pigeon allergy, pollen allergy, rhinitis, rhus tree allergy, salicylate sensitivity, sinusitis, skin rash, sparrow allergy, turkey allergy, ucaria, and yeast allergy.

The term "infectious diseases" includes any clinically evident disease resulting from the presence of a pathogenic microbial agent, including but not limited to viruses, bacteria, protozoa, parasites and fungi. The term "infectious diseases" includes but is not limited to AIDS, AIDS related complex, chickenpox, common cold, cytomegalovirus infection, colorado tick fever, dengue fever, ebola hemorrhagic fever, hand, foot and mouth disease, hepatitis, herpes simplex, herpes zoster, HPV, influenza (flu), lassa fever, measles, marburg hemorrhagic fever, infectious mononucleosis, mumps, norovirus, poliomyelitis, progressive multifocal leukencephalopathy, rabies, rubella, SARS, smallpox (variola), viral encephalitis, viral gastroenteritis, viral meningitis, viral pneumonia, west nile disease, yellow fever, anthrax, bacterial meningitis, botulism, brucellosis, campylobacteriosis, cat scratch disease, cholera, diphtheria, epidemic typhus, gonorrhea, impetigo-legionellosis, leprosy (hansen's disease), leptospirosis, listeriosis, lyme disease, melioidosis, rheumatic fever; MRSA infection, nocardiosis, pertussis (Whooping Cough), plague, pneumococcal pneumonia, psittacosis, Q fever, rocky mountain spotted fever (RMSF), salmonellosis, scarlet fever, shigellosis, syphilis, tetanus, trachoma, tuberculosis, tularemia, typhoid fever, typhus—urinary tract infections, african trypanosomiasis, amebiasis, ascariasis, babesiosis, chagas disease, clonorchiasis, cryptosporidiosis, cysticercosis, diphyllobothriasis, dracunculiasis, echinococcosis, enterobiasis, fascioliasis, fasciolopsiasis, filariasis, free-living amebic infection, giardiasis, gnathostomiasis, hymenolepiasis, isosporiasis, kala-azar, leishmaniasis, malaria, metagonimiasis, myiasis, onchocerciasis, pediculosis, pinworm infection, scabies, schistosomiasis, taeniasis, toxocariasis, toxoplasmosis, trichinellosis, trichinosis, trichuriasis, trichomoniasis, trypanosomiasis, aspergillosis, blastomycosis, candidiasis, coccidioidomycosis, cryptococcosis, histoplasmosis, tinea pedis, transmissible spongiform encephalopathy, bovine spongiform encephalopathy, creutzfeldt-Jakob disease, kuru, fatal familial insomnia, and alpers syndrome.

The term "autoimmune disease" includes all forms of disease wherein the immune system reacts to a self antigen, including but not limited to rheumatoid arthritis, type 1 diabetes mellitus, hashimoto's thyroiditis, graves' disease, scleroderma, coeliac disease, crohn's disease, ulcerative colitis, sjogren's syndrome, multiple sclerosis, guillain-barre syndrome, goodpasture's syndrome, addison's disease, wegener's granulomatosis, primary biliary sclerosis, sclerosing cholangitis, autoimmune hepatitis, rheumatoid arthritis, autoimmune thyroid diseases, systemic lupus erythematosus, psoriasis, psoriatic arthritis, sympathetic ophthalmitis, autoimmune neuropathies, autoimmune oophoritis, autoimmune orchitis, autoimmune lymphoproliferative syndrome, antiphospholipid syndrome, lupus, polyendocrine deficiency syndrome, polyendocrine deficiency syndrome type 1, polyendocrine deficiency syndrome type 2, immune thrombocytopenic purpura, pernicious anemia, myasthenia gravis, mixed connective tissue disease, primary glomerulonephritis, vitiligo, autoimmune uveitis autoimmune hemolytic anemia, autoimmune thrombocytopenia, celiac disease, aermatitis herpetiformis, emphigus, pemphigus vulgaris, pemphigus foliaceus, bullous pemphigoid, autoimmune myocarditis, autoimmune vasculitis, autoimmune eye diseases, alopecia areata, autoimmune atherosclerosis, behcet's disease, autoimmune myelopathy, autoimmune hemophilia, autoimmune interstitial cystitis, autoimmune diabetes insipidus, autoimmune endometriosis, relapsing polychondritis, ankylosing spondylitis, autoimmune urticaria, paraneoplastic autoimmune syndromes, dermatomyositis, miller fisher syndrome, and IgA nephropathy.

The invention also provides an antibody or an antibody fragment produced by any of the methods of the invention for use in the manufacture of a medicament for the treatment of allergy, infectious condition or disease and autoimmune condition or disease.

The invention further provides a method of treating allergy, infectious condition or disease and autoimmune condition or disease, comprising administering an antibody or antibody fragment produced by any of the methods of the invention.

The invention also includes formulating an antibody or antibody fragment produced by any of the methods of the invention, or a nucleic acid encoding such an antibody or antibody fragment into a pharmaceutically acceptable composition. In one embodiment, the pharmaceutical composition may comprise one or more of the isolated antibodies or antibody fragments produced by any of the methods of the invention. In another embodiment, the pharmaceutical composition may comprise 2, 3, 4, 5, or more of the isolated antibodies or antibody fragments produced by any of the methods of the invention.

A pharmaceutical composition may also contain a pharmaceutically acceptable carrier to allow administration. The carrier should not itself induce the production of antibodies harmful to the individual receiving the composition and should not be toxic. Suitable carriers may include large, slowly metabolised macromolecules such as proteins, polypeptides, liposomes, polysaccharides, polylactic acids, polyglycolic acids, polymeric amino acids, amino acid copolymers and inactive virus particles.

In certain embodiments, pharmaceutically acceptable salts may be used, for example mineral acid salts, such as hydrochlorides, hydrobromides, phosphates and sulphates, salts of organic acids, such as acetates, propionates, malonates and benzoates.

In some embodiments, the pharmaceutical composition may also contain liquids such as water, saline, glycerol and ethanol. Additionally, auxiliary substances, such as wetting or emulsifying agents or pH buffering substances, may be present in the composition, and may enable the pharmaceutical compositions to be formulated as tablets, pills, dragees, capsules, liquids, gels, syrups, slurries and suspensions, for ingestion by the patient.

The pharmaceutical composition may be administered by any number of routes including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes.

The pharmaceutical composition may have a pH between 5.5 and 8.5, in some embodiments between 6 and 8, and in further embodiments about 7. The pH may be maintained by the use of a buffer. The composition may be sterile and/or pyrogen free. The composition may be isotonic with respect to humans.

In another embodiment, an isolated antibody or antibody fragment produced by any of the methods of the invention may be combined with a diagnostic excipient to form a diagnostic reagent. In one embodiment, the diagnostic reagent may comprise one or more of the isolated antibodies or antibody fragments produced by any of the methods of the invention. For example, the diagnostic reagent may comprise 2, 3, 4, 5, or more of the isolated antibodies or antibody fragments produced by any of the methods of the invention.

The diagnostic excipient may comprise a pharmaceutically acceptable carrier to allow administration of the diagnostic reagent to the patient. The carrier should not itself induce the production of antibodies harmful to the individual receiving the composition and should not be toxic. Suitable carriers may include large, slowly metabolised macromolecules such as proteins, polypeptides, liposomes, polysaccharides, polylactic acids, polyglycolic acids, polymeric amino acids, amino acid copolymers and inactive virus particles.

In certain embodiments, pharmaceutically acceptable salts may be used, for example mineral acid salts, such as hydrochlorides, hydrobromides, phosphates and sulphates, alts of organic acids, such as acetates, propionates, malonates and benzoates.

In some embodiments, the pharmaceutical reagent may also contain liquids such as water, saline, glycerol and ethanol. Additionally, auxiliary substances, such as wetting or emulsifying agents or pH buffering substances, may be present.

The diagnostic reagent may be used in diagnosis in vivo, in vitro or ex vivo. For in vivo use, the diagnostic reagent may be administered by any number of routes including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes.

Diagnostic reagents may have a pH between 5.5 and 8.5, in some embodiments between 6 and 8, and in further embodiments about 7. The pH may be maintained by the use of a buffer. The composition may be sterile and/or pyrogen free. The diagnostic reagent may be isotonic with respect to humans.

In one embodiment, the diagnostic reagent may include labelling the antibody. The label may be selected from a fluorescent label, a radio label, a hapten and a biological label, including an enzymic label.

The diagnostic reagent may be used to ascertain the presence or absence of a particular antigen. This information can be extrapolated to determine the presence or absence of a particular pathogen, and therefore of a particular disorder or disease. In one aspect of the invention, the disease may be an allergy, an infectious condition or disease or an autoimmune condition or disease. Information achieved using the diagnostic reagent may be used to determine an appropriate course of treatment for a particular patient. In particular, the diagnostic reagent may be used to determine the presence or absence of allergens.

The term "allergen" includes any non-parasitic antigen capable of stimulating a hypersensitivity reaction in an individual, including but not limited to cats, fur, dander, cockroach calyx, wool, dust mites, dust mite excretion, penicillin, sulfonamides, salicylates, anaesthetics including local anaesthetics, celery, celeriac, corn, maize, wheat, eggs, albumen, fruit, pumpkin, legumes, beans, peas, nuts, peanuts, soybeans, milk, seafood, sesame, soy, tree nuts, pecans, almonds, insect stings, bee sting venom, wasp sting venom, mosquito stings, mould spores, latex, metal, plant pollens, grass including ryegrass and timothy-grass, weeds including ragweed, plantago, nettle, artemisia vulgaris, chenopodium album and sorrel, and trees, including birch, alder, hazel, hornbeam, aesculus, willow, poplar, platanus, tilia, olea, Ashe juniper.

Use of Isolated Antibodies in Protein Purification

The invention also includes a method of immobilising an isolated antibody or antibody fragment produced by any of the methods of the invention, onto a solid support. The term "solid support" includes both solid and semi-solid supports, and encompasses any support upon which can be used to immobilise the isolated antibody or antibody fragment. The solid support may include, a gel, mesh, bead including glass spheres or magnetic beads, column, tube, well of a microtitre plate, or plastic sheet. The immobilised antibody or antibody fragment produced by any of the methods of the invention may be used in protein purification. In one embodiment, the immobilised antibody may be used in immunoaffinity chromatography. A solution comprising the protein of interest may be applied to a solid support comprising the immobilised antibodies or antibody fragments produced by any of the methods of the invention, and which are known to have specificity for the protein of interest. The antibody or antibody fragments may, for example, be immobilised on beads, that can, in some embodiments, be held within a column.

General

The term "comprising" encompasses "including" as well as "consisting" e.g. a composition "comprising" X may consist exclusively of X or may include something additional e.g. X +Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x+10%.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

As used herein, reference to "treatment" of a patient is intended to include prevention and prophylaxis as well as therapy. The term "patient" means all mammals including humans. Generally, the patient is a human.

EXAMPLES

Exemplary embodiments of the present invention are provided in the following examples. The following examples are presented only by way of illustration and to assist one of ordinary skill in using the invention. The examples are not intended in any way to limit the scope of the invention.

Example 1

Plasma Cells in Mesenchymal Stromal Cell Culture

The inventors observed that primary cultures of human mesenchymal stromal cells established from normal bone marrow according to standard methods (Pittenger et al, 1999, *Science* 284:143-147; Bieback et al, 2004 *Stem cells* 22:625-634; Dominici et al, 2006, *Cytotherapy* 8:315-317; Sotiropoulou et al 2006, *Stem Cells* 24:462-471) contained antibody secreting cells. These cells were detected by ELISPOT, and identified as plasma cells. The plasma cells in the mesenchymal stromal cell culture were still detectable after 3 weeks in vitro (data not shown).

Example 2

Culture of Human Plasma Cells for up to 50 Days

In order to develop a culture system where individual plasma cells could be kept alive so that the antibody produced could accumulate as a function of the culture time, the inventors tested different sources of primary mesenchymal stromal cells prepared according to standard methods.

Briefly, tissue culture flasks were pre-coated with FCS for 1 hour. Bone marrow cells were allowed to adhere overnight in complete IMDM medium supplemented with 30% FCS and $10^{-8}$M Dexamethasone. The non adherent cells were washed out and the adherent cells were cultured in complete DMEM-10% FCS. Three out of the seven lines tested supported survival of human plasma cells, but stopped proliferating after a few passages. In subsequent experiments, mesenchymal stromal cells immortalized by transduction with the telomerase reverse transcriptase gene (MSC-TERT) were used. These cells were those isolated by Mihara et al. (*Br J Haematol* 2003, 120, 846-849).

Peripheral blood mononuclear cells were stained with PE-labelled anti-CD138 monoclonal antibody, enriched using anti-PE micro beads (Miltenyi) and further purified by cell sorting to isolate CD138-positive cells. The number of IgG-secreting plasma cells recovered was determined using an isotype-specific ELISPOT. Different numbers of CD138-positive cells were seeded on mesenchymal stromal cell monolayer in 96-well culture plates with RPMI 1640 supplemented with 10% fetal calf serum (Hyclone), non essential amino acids, pyruvate and glutamax (GIBCO). Based on ELISPOT performed at the time of plating, the culture represented in FIG. 1 contained seven IgG-secreting cells. Half of the culture supernatant was collected at different time points and replaced with fresh medium. Furthermore on day 18 and 34 the medium was completely removed and substituted with fresh one. The daily rate of IgG production per culture and the estimated daily rate of IgG production per plasma cell were determined. As shown in FIG. 1, the amount of IgG produced by a culture population of the present invention of approximately 7 cells increased as a linear function of the time of culture over 50 days, consistent with a rate of production of 676 pg/day and an estimated production of 96 pg/cell/day.

Example 3

Culture of Individual Plasma Cells for 3 Weeks

Figure 2:
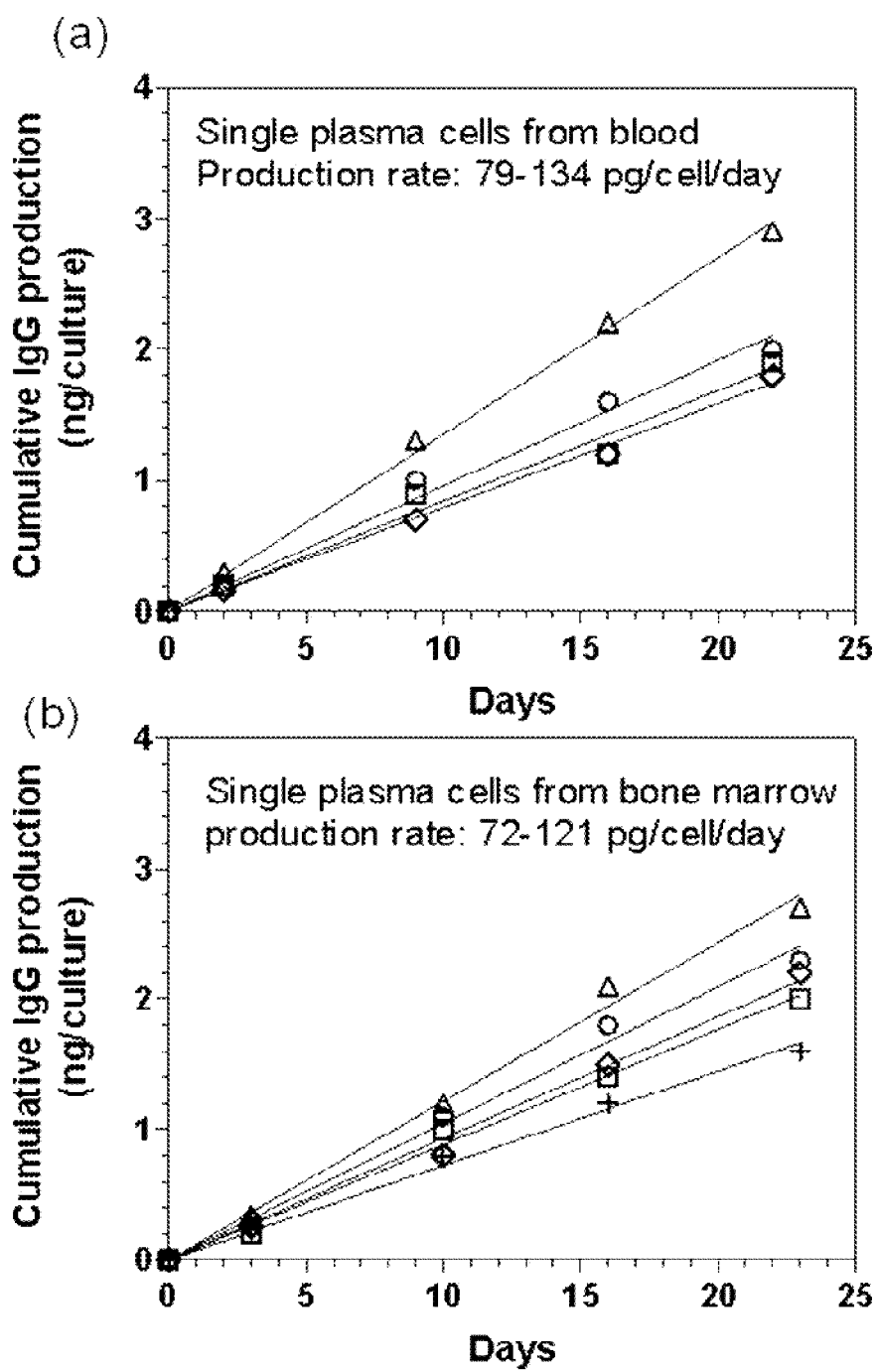
FIG. 2 shows the cumulative production of IgG by CD138+ plasma cells in cultures containing single plasma cells isolated from (A) peripheral blood and (B) bone marrow.

Plasma cells from peripheral blood or bone marrow were isolated using PE-conjugated anti-CD138 antibody followed by anti-PE microbeads and cell sorting and were seeded on mesenchymal stromal cell monolayers at 0.5 cells/well in 96-well plates. IgG containing cultures were monitored for a period of 22-23 days by regular sampling. Medium was exchanged on day 16. The rate of IgG production in monoclonal cultures was constant, ranging from 72 to 134 pg/cell/day over the entire period of culture (FIG. 2a, peripheral blood derived (4 cultures); FIG. 2b, bone marrow derived (5 cultures)).

In five limiting dilution experiments, the plating efficiency of blood and bone marrow plasma cells ranged from 30% to 65% (data not shown). In addition, plasma cells retrieved from polyclonal cultures could be re-plated in single cell cultures where they maintained constant rate of Ig secretion (data not shown). The linear accumulation of IgG is consistent with preservation of individual cells secreting IgG at a constantly high rate. IgG production by cultured plasma cells was not affected by irradiation at a level that completely abolished proliferation and differentiation of memory B cells stimulated by TLR agonists (data not shown).

Example 4

Culture of Plasma Cells Producing IgG, IgA, IgM and IgE

Figure 3:
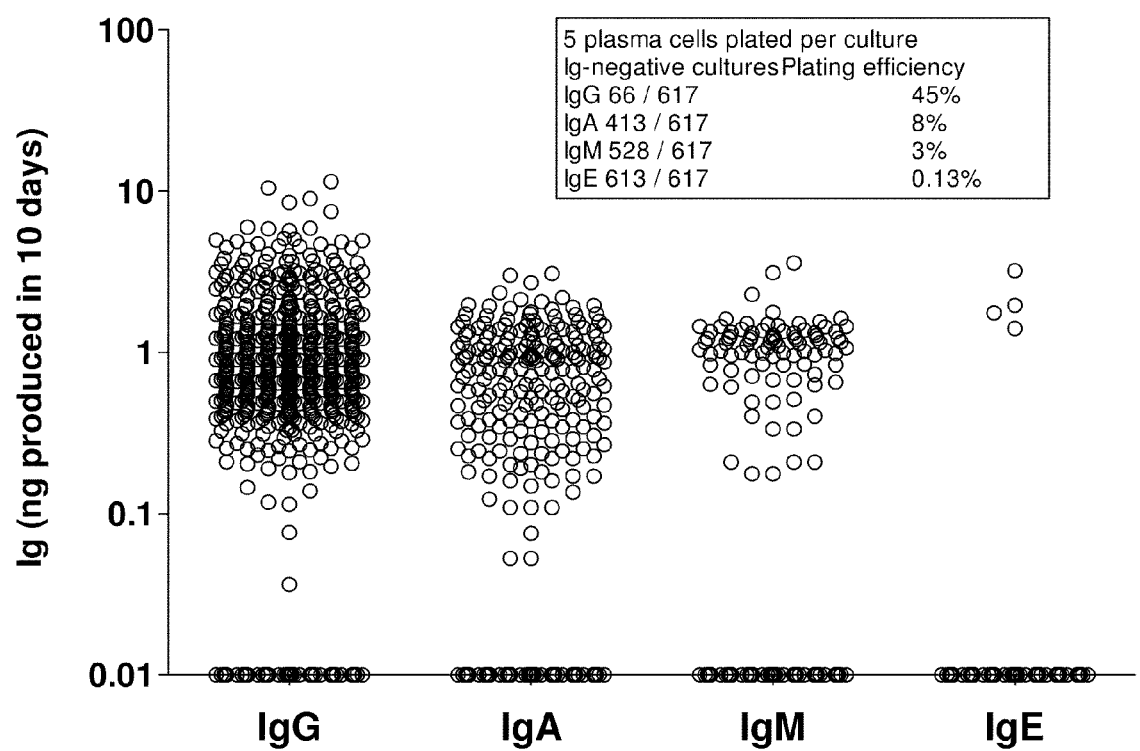
FIG. 3 shows the results of testing the day 10-culture supernatants of CD138-high plasma cells isolated from peripheral blood and cultured on monolayers of mesenchymal stromal cell for the presence of IgG, IgA, IgM and IgE.

Peripheral blood CD138-positive cells producing IgG, IgA, IgM and IgE were isolated from a healthy donor and plated at 5 cells/well in 384-well plates containing mesenchymal stromal cell monolayers in 617 replicate cultures. The day 10 culture supernatants were tested for the presence of IgG, IgA, IgM and IgE using isotype-specific ELISA. The total amount of the four isotypes was measured in the culture supernatants (see FIG. 3). The median value of productivity for IgG, IgA, IgM and IgE plasma cells was 860, 770, 1100 and 1800 pg in 10 days, i.e., 86, 77, 110 and 180 pg/cell/day, respectively.

Example 5

Efficiency of Plasma Cell Survival in vitro

Figure 4:
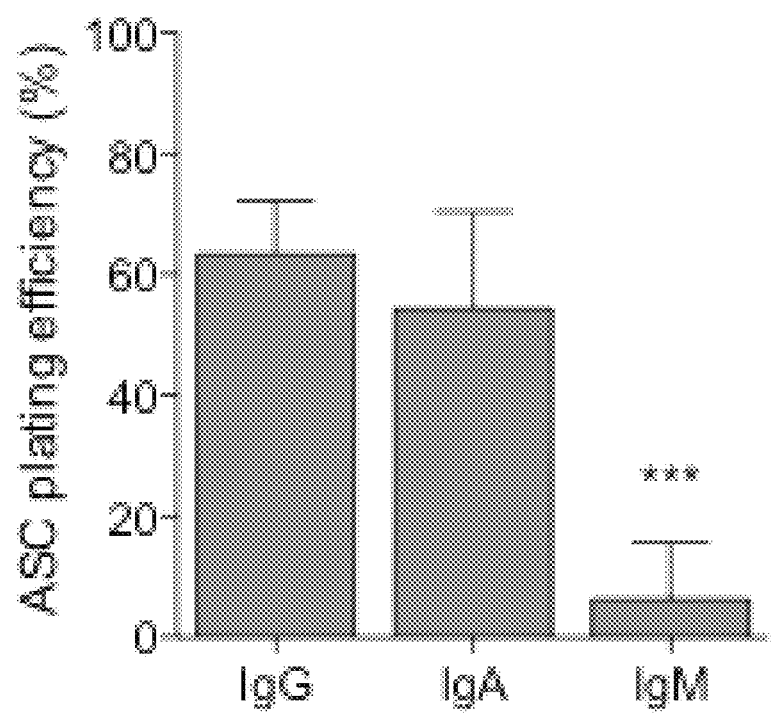
FIG. 4 shows the plating efficiency of antibody-secreting cells (ASC) producing IgG, IgA or IgM antibodies when cultured on hMSC-TERT cells and expressed as the percentage of plasma cells that survive long enough to produce detectable amounts of antibody in the supernatant.

Peripheral blood derived human plasma cells were isolated from seven donors according to CD138 expression and seeded at 1 or 25 cells/well. The number of IgG-, IgA- and IgM-antibody secreting cells at the beginning of cultures was calculated by isotype specific ELISPOT. Plating efficiency was calculated on IgG-, IgA- and IgM-antibody secreting cells according to Poisson distribution analysis and ranged from 50% to 74% for IgG, from 31% to 78% for IgA and from 0 to 26% for IgM (see FIG. 4). In addition, plasma cells retrieved from polyclonal cultures could be re-plated in single cell cultures where they maintained constant rate of Ig secretion (data not shown).

Example 6

Isolation of Rare IgE Monoclonal Antibodies

Plasma cells were isolated from peripheral blood of an allergic individual and plated at 1 cell/well on hMSC-TERT monolayers in ten 384-well microplates. Five culture supernatants scored positive for IgE production. The IgE-positive cultures were subjected to RT-PCR and two paired VH/VL genes were retrieved and sequenced (Table 1). The V genes were cloned into expression vectors for expression of a light chain (kappa or lambda) or of a human IgG1 or IgE heavy chain according to the method described in Wardemann et al., (*Science* 301, 1374-1377, 2003). The IgG or IgE antibodies were produced by transient transfection of 293T cells. This example illustrates the possibility to retrieve rare plasma cells and to isolate representative IgE monoclonal antibodies.

TABLE 1

Two IgE monoclonal antibodies retrieved from circulating plasma cells.

| | | Heavy Chain | | | | | | Light Chain | | | |
|---|---|---|---|---|---|---|---|---|---|---|---|
| Clone | Isotype | V gene | N1 nt | D gene | N2 nt | J gene | SHM nt (aa) | V gene | N nt | J gene | SHM nt (aa) |
| IgE1 | IgE, λ | 3-9*01 | 4 | 2-15*01 | 5 | 4*02 | 30 (16) | 2-14*01 | 5 | 2*01 | 18 (12) |
| IgE2 | IgE, κ | 3-15*01 | 0 | 2-2*01 | 9 | 6*03 | 15 (7) | 3-11*01 | 1 | 5*01 | 8 (7) |

SHM nt: somatic hypermutation nucleotide; aa: amino acid

Example 7

Figure 5:
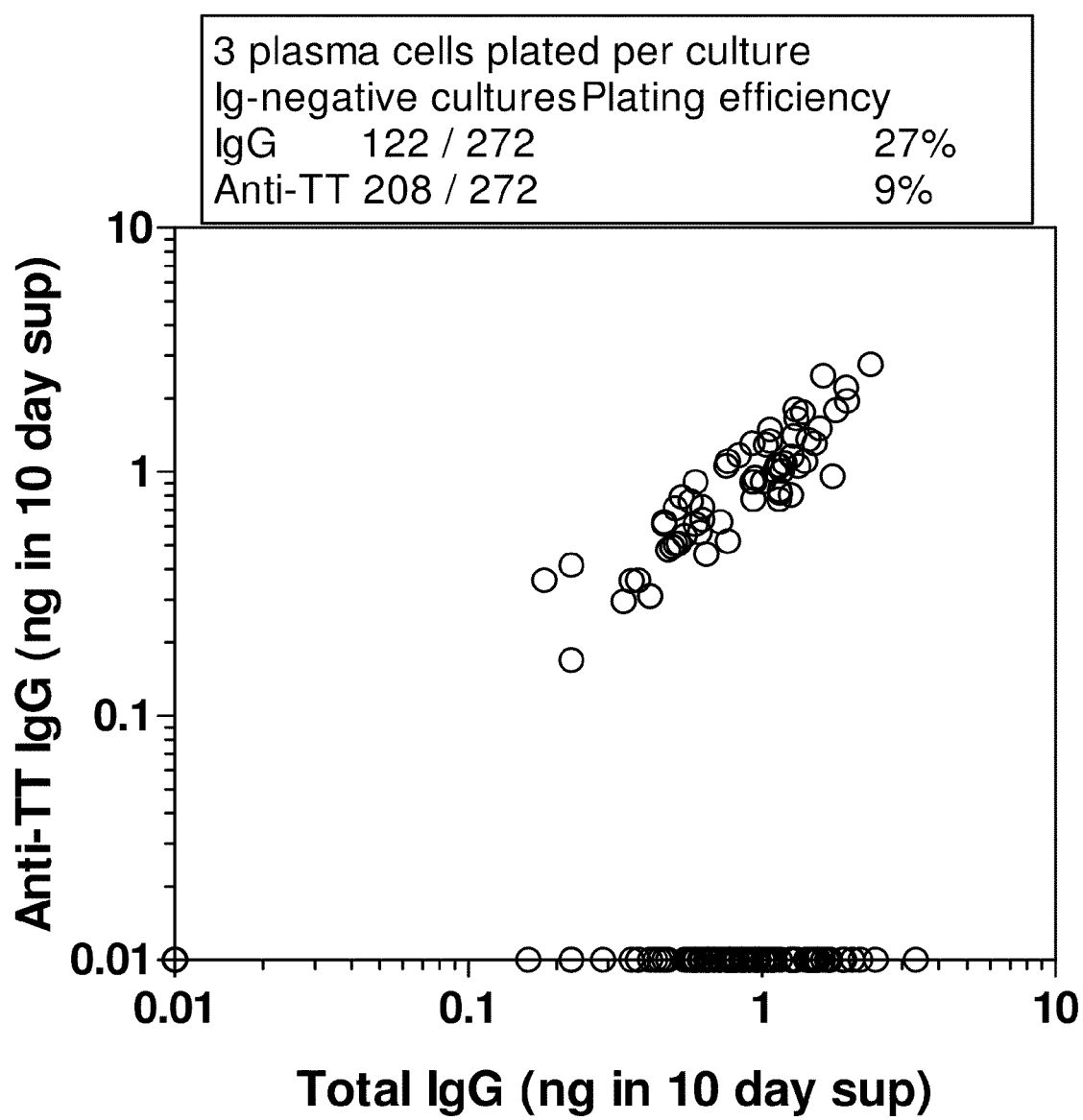
FIG. 5 shows the identification of plasma cells secreting tetanus toxoid-specific IgG from plasma cells isolated from peripheral blood collected 7 days after tetanus toxoid (TT) booster immunization.

Isolation of Antigen-Specific Monoclonal Antibodies from Plasma Cells Cultured in the Presence of Mesenchymal Stromal Cells Plasma cells were isolated from peripheral blood of a donor 7 days after booster vaccination with tetanus toxoid (TT) and seeded in clonal conditions on MSC-TERT monolayers in 384 well microplates. The day 10 culture supernatants were analysed for the presence of total IgG (ng/culture) as well as TT-specific IgG antibodies (OD405) and monoclonal cultures producing TT-specific antibodies were identified (see FIG. 5). This example illustrates the possibility of identifying large numbers of antigen-specific plasma cells following a booster immunization.

Example 8

Isolation of a Potent and Broadly Reactive Influenza A Neutralizing Antibody from Plasma Cells Cultured in the Presence of IL-6

CD138-positive cells from a donor immunized 7 days before with a seasonal influenza vaccine were seeded in sixteen 384 well-plates at 0.5 cells/well in the presence of 10 ng/ml IL-6. On day 6 and 8 the culture supernatants were tested in three parallel ELISAs using as antigens recombinant H5 or H9 baculovirus-derived recombinant hemagglutinins (HA) and the irrelevant antigen tetanus toxoid (TT). Out of the 4,928 culture supernatants screened, 12 bound to H5 HA, 25 to H9 HA and 54 to both H5 and H9. Some of the latter with highest OD signal were subjected to RT-PCR and two paired VH/VL genes were retrieved. The two monoclonal antibodies, FI6 and FI28, shared most V, D and J gene fragments (IGHV3-30*01, IGHD3-9*01, IGHJ4*02 and IGKV4-1*01), but differed in the N regions, in the IGKJ usage and in the pattern of somatic mutations and were therefore not clonally related.

The V genes of FI6 and FI28 were cloned into expression vectors and recombinant antibodies were produced by transfecting 293T cells. Their specificity was investigated by ELISA using a panel of recombinant HAs belonging to different subtypes (Table 2). FI6 bound all influenza A HA subtypes tested including group 1 (H1, H5 and H9) and group 2 (H3 and H7), while did not bind HA from influenza B. In contrast FI28 bound only to the group 1 HAs.

TABLE 2

Binding of plasma cell derived human monoclonal antibodies to influenza HAs

| | Binding to HA by ELISA (% of subtype specific control antibodies) | | | | |
|---|---|---|---|---|---|
| | H1 A/NC/ 20/99 | H3 A/BR/ 10/07 | H5 A/VN/ 1203/04 | H7 A/NL/ 219/03 | H9 A/HK/ 1073/99 |
| FI6 | 85.9 | 68.5 | 73.7 | 87.9 | 98.7 |
| FI28 | 59.4 | 1.3 | 46.3 | −0.5 | 87.7 |

We next tested FI6 and FI28 for their capacity to neutralize group 1 and group 2 influenza A subtypes using pseudoviruses as well as infectious viruses. Remarkably FI6 neutralized all pseudoviruses tested, including six H5 isolates belonging to the antigenically divergent clades 0, 1, 2.1, 2.2 and 2.3, and two H7 avian isolates (Table 3). In addition FI6 neutralized all infectious viruses tested, including two H3N2 viruses and four H1N1 viruses spanning a 70 year period up to the recent pandemic swine-origin H1N1 isolate A/Cal/04/09 (Table 4). In contrast FI28 neutralized all H5 pseudoviruses but failed to neutralize H7 pseudoviruses as well as all the infectious viruses tested (Tables 3 and 4).

TABLE 3

Neutralization of H5 and H7 pseudotypes by human monoclonal antibodies

| | Neutralization of HA-pseudotypes (IC90, µg/ml) | | | | | | | |
|---|---|---|---|---|---|---|---|---|
| | H5N1 | | | | | | H7N1 | |
| | A/HK/ 491/97 | A/HK/ 213/03 | A/VN/ 1203/04 | A/INDO/ 5/05 | A/WS/ MONG/05 | A/AH/ 1/05 | A/ck/IT/ 13474/99 | A/ck/FPV/ Ro/34 |
| FI6 | 0.07 | 0.02 | 0.02 | 0.31 | 0.03 | 0.05 | 1.87 | 0.09 |
| FI28 | 0.05 | 0.33 | 0.02 | 0.35 | 0.04 | 0.05 | >100 | >100 |

TABLE 4

Neutralization of influenza viruses by human monoclonal antibodies.

| | Neutralization of infectious viruses (IC50, µg/ml) | | | | | |
|---|---|---|---|---|---|---|
| | H1N1 | | | | H3N2 | |
| | A/PR/ 8/34 | A/NC/ 20/99 | A/SI/ 3/06 | A/CA/ 4/09 | A/CA/ 7/04 | A/WI/ 67/05 |
| FI6 | 2.2 | 6.3 | 8.8 | 12.5 | 7.9 | 12.5 |
| FI28 | >100 | >100 | >100 | nd | >100 | >100 | nd, not done
nd, not done

It should be noted that the method detailed above delivers 50 µl of monoclonal antibody at approximately 8-16 ng/ml in 5-10 days. This volume and antibody concentration are sufficient to perform multiple assays. These assays comprise not only binding assays such as ELISA (that can be performed in a standard shallow 384 plate format using 5 µl), but also functional assays, such as pseudotyped neutralization, which are in the range of sensitivity (see Table 3). Importantly, the ability to perform multiple parallel assays is essential to rapidly identify rare plasma cells that secrete antibodies capable of binding to multiple antigen variants.

Example 9

Figure 6:
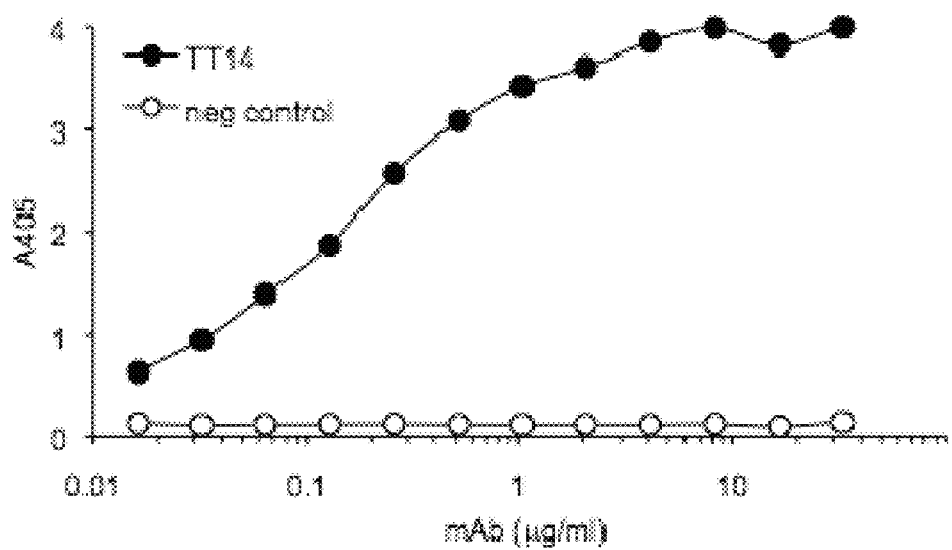
FIG. 6 shows the binding to tetanus toxoid of a recombinant antibody produced by cloning and expression of VH and VL genes retrieved from a cultured plasma cell isolated from the blood of a donor 10 years after vaccination with tetanus toxoid.

Isolation of a Tetanus Toxoid-Specific Monoclonal Antibody from Cultured Plasma Cells Isolated from Peripheral Blood Ten Years after Vaccination CD138+ HLA-DR+CD62L+plasma cells were isolated by cell sorting from the peripheral blood of a donor 10 years after tetanus-toxoid (TT) vaccination. A total of 1,700 cells were seeded at 0.5 cells/well in 384-well microplates and cell culture supernatants were screened at day 7 by ELISA for the presence of tetanus-toxoid-specific IgG antibodies. One tetanus toxoid-specific culture was identified and on day 8 VH/VL genes were retrieved by RT-PCR and sequenced (see Table 5). The genes were cloned into expression vectors and the recombinant antibody (TT14) was produced by transient transfection of 293T cells. The antibody was tested at different concentrations for binding to tetanus toxoid or to an unrelated antigen (negative control) by ELISA (see FIG. 6).

TABLE 5

Tetanus toxoid-specific monoclonal antibody retrieved from circulating plasma cells 10 years after vaccination

| | | Heavy Chain | | | | Light Chain | | |
|---|---|---|---|---|---|---|---|---|
| Clone | Isotype | V gene | D gene | J gene | SHM nt (aa) | V gene | J gene | SHM nt (aa) |
| TT14 | IgG4, 1 | 1-2*02 | 6-19*01 | 4*02 | 17 (13) | 7-46*01 | 3*02 | 9 (7) |

SHM nt: somatic hypermutation nucleotide; aa: amino acid

It should be noted that there are alternative ways of implementing the present invention and that various modifications can be made without departing from the scope and spirit of the invention. Accordingly, the present embodiments are to be considered as illustrative and not restrictive, and the invention is not to be limited to the details given herein, but may be modified within the scope and equivalents of the appended claims.

The invention claimed is:

1. A method of producing an antibody for 10 or more days comprising:
   culturing plasma cells in the presence of IL-6 or mesenchymal stromal cells in limited numbers and obtaining said antibody therefrom, wherein the number of cultured plasma cells is 10 or less, and wherein IL-6 or mesenchymal stromal cells is the only exogenous survival-prolonging component present in the culture.

2. The method of claim 1, wherein the number of cultured plasma cells is 1.

3. The method of claim 1, wherein the antibody is a human antibody and the plasma cells are human plasma cells.

4. The method of claim 2, wherein the antibody is a human antibody and the plasma cells are human plasma cells.

5. The method of claim 1, wherein-survival of the cultured plasma cells is prolonged for sufficient time such that the antibody is produced in quantities needed for characterization of the antibody.

6. The method of claim 2, wherein-survival of the cultured plasma cells is prolonged for sufficient time such that the antibody is produced in quantities needed for characterization of the antibody.

7. The method of claim 5, further comprising characterisation of the antibody or antibody fragment, wherein characterization of the antibody or antibody fragment comprises performing functional assays to determine the function of the antibody or antibody fragment, binding assays to determine the binding specificity of the antibody or antibody fragment or the epitope recognized by the antibody or antibody fragment, and/or neutralization assays to determine the ability of the antibody or antibody fragment to neutralize a toxin or a pathogen.

8. The method of claim 6, further comprising characterisation of the antibody or antibody fragment, wherein characterization of the antibody or antibody fragment comprises performing functional assays to determine the function of the antibody or antibody fragment, binding assays to determine the binding specificity of the antibody or antibody fragment or the epitope recognized by the antibody or antibody fragment, and/or neutralization assays to determine the ability of the antibody or antibody fragment to neutralize a toxin or a pathogen.

9. The method of claim 5, further comprising isolating the antibody from the culture medium.

10. The method of claim 6, further comprising isolating the antibody from the culture medium.

11. The method of claim 5, wherein survival of the plasma cells is prolonged for at least 20 days, or at least 30 days.

12. The method of claim 6, wherein survival of the plasma cells is prolonged for at least 20 days, or at least 30 days.

13. A method of producing an antibody or an antibody fragment, comprising the steps of:
   a. culturing a limited number of plasma cells according to the method of claim 1;
   b. identifying cultures producing an antibody with a desired characteristic;
   c. isolating nucleic acid encoding the antibody produced; and
   d. expressing the nucleic acid in a host cell.

14. A method of producing a monoclonal antibody or an antibody fragment, comprising the steps of:
   a. culturing plasma cells in a single cell culture according to the method of claim 2;
   b. identifying cultures producing an antibody with a desired characteristic;
   c. isolating nucleic acid encoding the antibody produced; and
   d. expressing the nucleic acid in a host cell.

15. The method of claim 13, further comprising characterisation of the antibody or antibody fragment, wherein characterization of the antibody or antibody fragment comprises performing functional assays to determine the function of the antibody or antibody fragment, binding assays to determine the binding specificity of the antibody or antibody fragment or the epitope recognized by the antibody or antibody fragment, and/or neutralization assays to determine the ability of the antibody or antibody fragment to neutralize a toxin or a pathogen.

16. The method of claim 14, further comprising characterisation of the antibody or antibody fragment, wherein characterization of the antibody or antibody fragment comprises performing functional assays to determine the function of the antibody or antibody fragment, binding assays to determine the binding specificity of the antibody or antibody fragment or the epitope recognized by the antibody or antibody fragment, and/or neutralization assays to determine the ability of the antibody or antibody fragment to neutralize a toxin or a pathogen.

17. The method of claim 1, wherein the plasma cells are cultured in culture medium for a duration of time sufficient for said plasma cells to release said antibody into said culture medium in quantities needed for characterization of said antibody.

18. The method of claim 2, wherein the plasma cells are cultured in culture medium for a duration of time sufficient for said plasma cells to release said antibody into said culture medium in quantities needed for characterization of said antibody.

19. The method of claim 1, wherein the number of cultured plasma cells is 5 or less.

20. A method of producing an antibody for 10 or more days comprising:
   culturing plasma cells in the presence of IL-6 or mesenchymal stromal cells in limited numbers and obtaining said antibody therefrom, wherein the number of cultured plasma cells is 100 or less, and wherein IL-6 or mesenchymal stromal cells is the only exogenous survival-prolonging component present in the culture.

21. A method of prolonging the life of plasma cells in culture for 10 or mode days comprising: culturing said plasma cells in medium comprising IL-6 or mesenchymal stromal cells, wherein the number of cultured plasma cells is 10 or less and wherein IL-6 or mesenchymal stromal cells is the only exogenous survival-prolonging component present in the culture.

* * * * *